US00PP16286P2

(12) United States Plant Patent
Mostul

(10) Patent No.: US PP16,286 P2
(45) Date of Patent: Feb. 21, 2006

(54) ***HIBISCUS* PLANT NAMED 'MAPLE SUGAR'**

(50) Latin Name: *Hibiscus acetosella*
Varietal Denomination: Maple Sugar

(75) Inventor: Burl Mostul, Portland, OR (US)

(73) Assignee: Rare Plant Research, Portland, OR (US)

( * ) Notice: Subject to any disclaimer, the term of this patent is extended or adjusted under 35 U.S.C. 154(b) by 2 days.

(21) Appl. No.: 10/955,491

(22) Filed: Sep. 30, 2004

(51) Int. Cl.
*A01H 5/00* (2006.01)

(52) U.S. Cl. ..... Plt./257
(58) Field of Classification Search ..... Plt./257
See application file for complete search history.

(56) References Cited

U.S. PATENT DOCUMENTS

PP9,311 P * 10/1995 Bost ..... Plt./257
PP11,772 P2 * 2/2001 Bergman ..... Plt./257
PP15,551 P2 * 2/2005 Bevelander ..... Plt./257

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct *Hibiscus* plant named 'Maple Sugar', characterized by its upright and outwardly spreading plant habit; relatively large burgundy-colored leaves; and burgundy-colored flowers.

1 Drawing Sheet

Botanical classification: *Hibiscus acetosella.*
Cultivar denomination: 'Maple Sugar'.

BACKGROUND OF THE INVENTION

The present invention relates to a new and distinct cultivar of *Hibiscus,* botanically known as *Hibiscus acetosella,* and hereinafter referred to by the name 'Maple Sugar'.

The new *Hibiscus* is a product of a planned breeding program conducted by the Inventor in Portland, Oreg. The objective of the breeding program is to create new *Hibiscus* cultivars with attractive leaf and flower coloration.

The new *Hibiscus* originated from a cross-pollination made by the Inventor in Mexico in October, 2000, of two unnamed selections of *Hibiscus acetosella,* not patented. The cultivar Maple Sugar was discovered and selected by the Inventor as a single flowering plant within the progeny of the stated cross-pollination in a controlled environment in Mexico in November, 2000.

Asexual reproduction of the new *Hibiscus* by vegetative cuttings in a controlled environment in Portland, Oreg. since December, 2000, has shown that the unique features of this new *Hibiscus* are stable and reproduced true to type in successive generations.

SUMMARY OF THE INVENTION

The cultivar Maple Sugar has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Maple Sugar'. These characteristics in combination distinguish 'Maple Sugar' as a new and distinct cultivar:

1. Upright and outwardly spreading plant habit.
2. Relatively large burgundy-colored leaves.
3. Burgundy-colored flowers.

Compared to plants of the parent selections, plants of the new *Hibiscus* have slightly larger leaves and more intense leaf and flower colors.

Compared to plants of the other selections and cultivars of *Hibiscus acetosella* known to the Inventor, plants of the new *Hibiscus* have slightly larger leaves and more intense leaf and flower colors.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photographs at the top left and right of the sheet comprise front and side perspective views of typical flowers of 'Maple Sugar'.

The photograph at the center of the sheet is a close-up view of typical flowers of 'Maple Sugar' with the corolla removed.

The photograph at the bottom of the sheet comprises a side perspective view of a typical plant of 'Maple Sugar'.

DETAILED BOTANICAL DESCRIPTION

The aforementioned photographs and following observations, measurements and values describe plants grown in an outdoor nursery in Bonsall, Calif. during the late spring under conditions which closely approximate commercial production. During the production of the plants, day temperatures ranged from 18° C. to 38° C. and night temperatures ranged from 13° C. to 18° C. Plants were about seven to eight weeks old when the photographs and the description were taken. Plants were pinched two times. In the description, color references are made to The Royal Horticultural Society Colour Chart, 1995 Edition, except where general terms of ordinary dictionary significance are used.

Botanical classification: *Hibiscus acetosella* cultivar Maple Sugar.

Parentage:

*Female or seed parent.*—Unnamed selection of *Hibiscus acetosella,* not patented.

*Male or pollen parent.*—Unnamed selection of *Hibiscus acetosella,* not patented.

Propagation:

*Type.*—By vegetative cuttings.

*Time to initiate roots, summer.*—About 10 days at temperatures of 35° C.

*Time to initiate roots, winter.*—About 15 days at temperatures of 25° C.

*Time to develop roots, summer.*—About 35 days at temperatures of 35° C.

*Time to develop roots, winter.*—About 45 days at temperatures of 25° C.

*Root description.*—Fibrous; freely branching; moderately dense; whitish in color.

Plant description:

*Plant form and growth habit.*—Perennial subshrub. Upright and outwardly spreading plant habit; open plant form; inverted triangle. Vigorous growth habit.

*Branching habit.*—About six lateral branches per plant; pinching enhances lateral branching.

*Plant height.*—About 52 cm.

*Plant diameter* (*area of spread*).—About 64 cm.

*Lateral branch description.*—Length: About 40 cm. Diameter: About 6 mm. Internode length: About 6.5 cm. Texture: Immature, slightly pubescent; mature, smooth. Color: 187A.

*Foliage description.*—Arrangement: Alternate, single. Length: About 7 cm. Width: About 8 cm. Shape: Three to five-lobed; lobes deeply dissected. Apex: Acute. Base: Acute to attenuate. Margin: Serrate to crenate; deeply incised; undulate. Texture, upper and lower surfaces: Smooth; glabrous. Venation pattern: Palmate. Color: Developing foliage, upper surface: 187A. Developing foliage, lower surface: 183A. Fully expanded foliage, upper surface: 200A with a slight dark olive green, 147A, cast. Fully expanded foliage, lower surface: More gray than 187A. Venation, upper and lower surfaces: 187A. Petiole: Length: About 6.5 cm. Diameter: About 3 mm. Texture, upper and lower surfaces: Rough. Color, upper surface: 187A. Color, lower surface: 183A. Leaf stipules: Quantity: Two per leaf. Length: About 1.2 cm. Width: About 4 mm. Shape: Linear. Color: 187A.

Flower description:

*Flower arrangement.*—Flowers arranged singly at terminal leaf axils. About one open flower and seven to eight flower buds per lateral branch. Flowers face mostly outward. Flowers not fragrant.

*Flower appearance.*—Rounded, dark burgundy-colored flowers. Flowers are open for about one day. Flowers persistent.

*Natural flowering season.*—Usually spring and summer or during periods of warm weather.

*Flower diameter.*—About 9.5 cm.

*Flower length* (*height*).—About 6.5 cm.

*Flower bud.*—Length: About 3.8 cm. Diameter: About 1.4 cm. Shape: Elliptical. Color: 187A.

*Petals.*—Arrangement: Corolla consists of five petals that are fused at base. Length: About 5.8 cm. Width: About 4 cm. Shape: Obovate. Apex: Rounded. Base: Attenuate. Margin: Entire; ruffled. Texture, upper and lower surface: Smooth, glabrous; velvety. Color: When opening and fully opened, upper surface: 187A. When opening and fully opened, lower surface: 187B.

*Sepals.*—Appearance: Five sepals fused into a tubular star-shaped calyx. Length: About 1.7 cm. Width: About 8 mm. Shape: Elliptical. Apex: Acute. Margin: Entire. Texture, upper surface: Smooth, glabrous. Texture, lower surface: Slightly coarse; pubescent. Color, upper surface: 148B tinted with 187D. Color, lower surface: 187C.

*Bracts.*—Appearance: About ten in a single whorl. Length: About 1.8 cm. Width: About 3 mm. Shape: Linear; clawed. Apex: Acute. Margin: Entire. Texture, upper and lower surfaces: Scattered pubescence towards margins. Color, upper and lower surfaces: 187A.

*Peduncles.*—Length: About 1 cm. Diameter: About 2 mm. Angle: About 45 to 60° from vertical. Strength: Strong, flexible. Texture: Smooth. Color: 187A.

*Reproductive organs.*—Androecium: Stamen number: About 30 per flower. Filament length: About 3 mm. Anther shape: Oval. Anther length: About 1 mm. Anther color: 187A. Amount of pollen: Scarce. Pollen color: 172A. Gynoecium: Quantity: One per flower. Pistil length: About 3 cm. Style length: About 2.1 cm. Style texture: Smooth, waxy. Style color: Close to 10D overlain with 59C. Stigma appearance: Five-parted, rounded. Stigma diameter: About 1 mm. Stigma color: 187A. Ovary color: Close to 10D overlain with 59C. Seed/fruit: Seed and fruit production has not been observed.

Temperature/tolerance: Plants of the new *Hibiscus* have been observed to tolerate temperatures from 0 to 42° C.

Disease tolerance: Plants of the new *Hibiscus* have not been observed to resistant to pathogens and pests common to *Hibiscus.*

It is claimed:

1. A new and distinct *Hibiscus* plant named 'Maple Sugar', as illustrated and described.

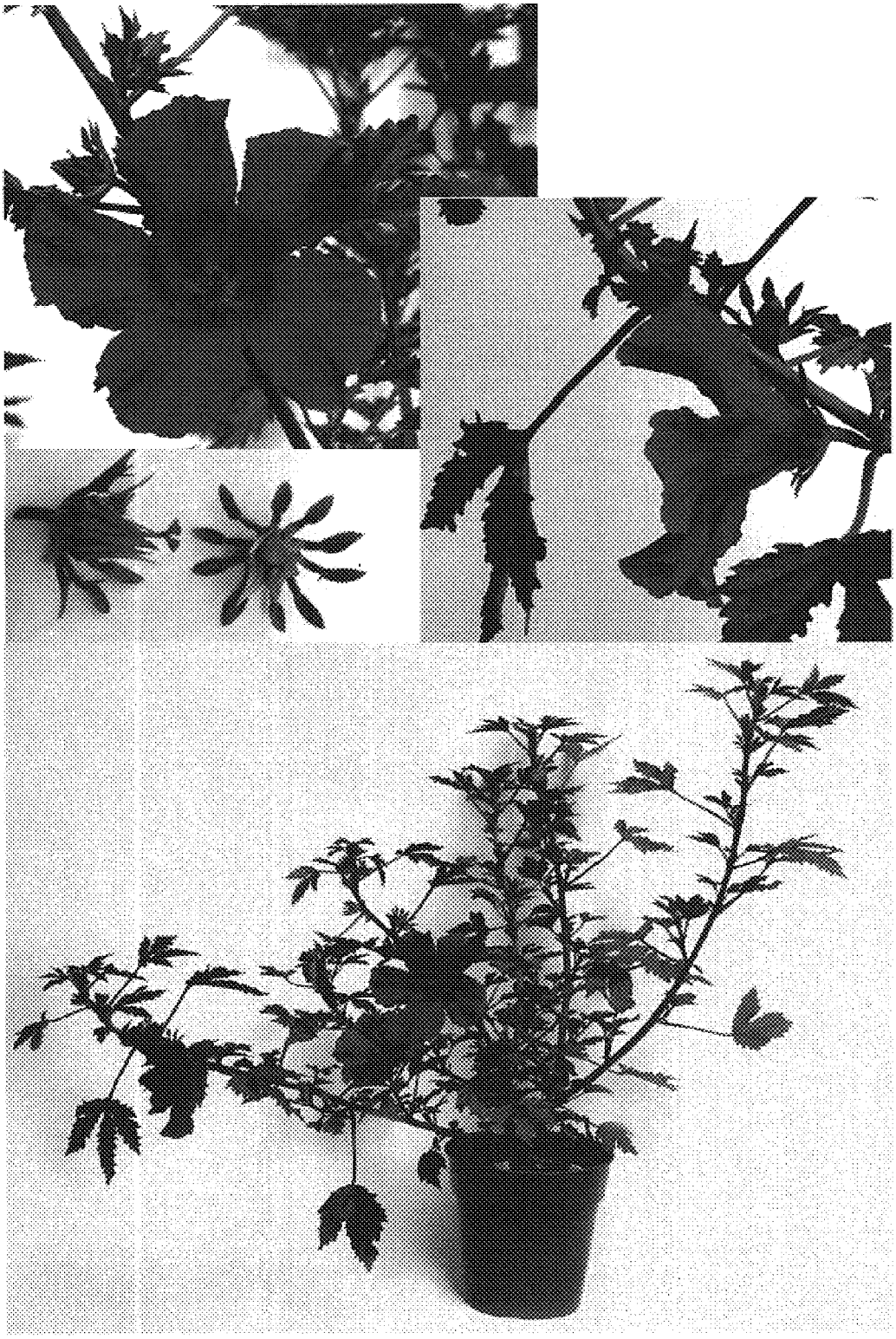

* * * * *